(12) United States Patent
Westphal et al.

(10) Patent No.: US 9,239,293 B2
(45) Date of Patent: Jan. 19, 2016

(54) MULTISPECTRAL ILLUMINATION DEVICE

(71) Applicant: Carl Zeiss Microscopy GmbH, Jena (DE)

(72) Inventors: Peter Westphal, Jena (DE); Daniel Bublitz, Rausdorf (DE)

(73) Assignee: Carl Zeiss Microscopy GmbH, Jena (DE)

(*) Notice: Subject to any disclaimer, the term of this patent is extended or adjusted under 35 U.S.C. 154(b) by 0 days.

(21) Appl. No.: 14/076,875

(22) Filed: Nov. 11, 2013

(65) Prior Publication Data

US 2014/0070106 A1  Mar. 13, 2014

Related U.S. Application Data

(63) Continuation of application No. 13/324,472, filed on Dec. 13, 2011, now Pat. No. 8,610,088, which is a continuation of application No. 12/083,980, filed as application No. PCT/EP2006/010745 on Nov. 9, 2006, now Pat. No. 8,097,865.

(30) Foreign Application Priority Data

Nov. 14, 2005 (DE) .......................... 10 2005 054 184

(51) Int. Cl.
*G02B 21/00* (2006.01)
*G01N 21/64* (2006.01)
(Continued)

(52) U.S. Cl.
CPC ...... *G01N 21/64* (2013.01); *F21V 9/08* (2013.01); *G01N 21/6458* (2013.01); *G02B 19/0028* (2013.01); *G02B 19/0066* (2013.01);
(Continued)

(58) Field of Classification Search
CPC combination set(s) only.
See application file for complete search history.

(56) References Cited

U.S. PATENT DOCUMENTS 5,317,162 A 5/1994 Pinsky et al.
5,343,038 A 8/1994 Nishiwaki et al.
(Continued)

FOREIGN PATENT DOCUMENTS

DE      103 61 176       7/2005
WO      WO 03/021212    3/2003

OTHER PUBLICATIONS

Translation of the Annex of the Written Notice of the International Search Authority (Form PCT/ISA/237), Feb. 23, 2007 (translation into English).
(Continued)

*Primary Examiner* — David Porta
*Assistant Examiner* — Djura Malevic
(74) *Attorney, Agent, or Firm* — Walter Ottesen P.A.

(57) ABSTRACT

An illumination device includes at least four semiconductor radiation sources (18) for emitting optical radiation in respectively different emission wavelength ranges. At least one color splitter (22.1, 22.2, 22.3), which is reflective for optical radiation of the respective semiconductor radiation source (18), is assigned to each of at least three of the semiconductor radiation sources (18). The semiconductor radiation sources (18) and the color splitters (22.1, 22.2, 22.3) are arranged such that the optical radiation, which is emitted in each case from each of the semiconductor radiation sources (18), is coupled into a common illumination beam path section (24). In each case, one collimating unit (20.1, 20.2, 20.3, 20.4), which collimates the optical radiation emitted by the respective semiconductor radiation source (18), is arranged in the beam path sections from the semiconductor radiation sources (18) to the color splitters (22.1, 22.2, 22.3).

22 Claims, 8 Drawing Sheets

(51) Int. Cl.
*G02B 21/06* (2006.01)
*G02B 21/16* (2006.01)
*G02B 27/10* (2006.01)
*G02B 27/14* (2006.01)
*G02B 19/00* (2006.01)
*F21V 9/08* (2006.01)

(52) U.S. Cl.
CPC ............ *G02B19/0095* (2013.01); *G02B 21/06* (2013.01); *G02B 21/16* (2013.01); *G02B 27/1006* (2013.01); *G02B 27/141* (2013.01); *G02B 27/145* (2013.01)

(56) References Cited

U.S. PATENT DOCUMENTS

| | | | |
|---|---|---|---|
| 5,537,247 A | 7/1996 | Xiao | |
| 5,844,707 A * | 12/1998 | Minakuchi et al. | 359/204.1 |
| 6,055,095 A | 4/2000 | Bawolek | |
| 6,096,272 A | 8/2000 | Clark et al. | |
| 6,134,365 A | 10/2000 | Colvin | |
| 6,211,955 B1 | 4/2001 | Basiji et al. | |
| 6,249,341 B1 | 6/2001 | Basiji et al. | |
| 6,365,920 B1 | 4/2002 | Abramov et al. | |
| 6,372,485 B1 | 4/2002 | Clark et al. | |
| 6,486,458 B1 * | 11/2002 | Schoeppe et al. | 250/205 |
| 6,674,573 B2 | 1/2004 | Suzuki | |
| 6,819,411 B1 | 11/2004 | Sharpe et al. | |
| 6,838,680 B2 | 1/2005 | Maher et al. | |
| 6,924,490 B2 | 8/2005 | Natori | |
| 7,154,111 B2 | 12/2006 | Shaver | |
| 7,440,183 B2 | 10/2008 | Bender | |
| 7,547,873 B2 | 6/2009 | Babayoff et al. | |
| 7,561,328 B2 | 7/2009 | Awamura et al. | |
| 7,561,329 B2 | 7/2009 | Zahniser et al. | |
| 7,586,677 B2 | 9/2009 | Bertschi et al. | |
| 8,625,097 B2 * | 1/2014 | Brukilacchio et al. | 356/417 |
| 2002/0071121 A1 * | 6/2002 | Ortyn et al. | 356/419 |
| 2002/0085274 A1 * | 7/2002 | Sasaki et al. | 359/385 |
| 2002/0104961 A1 * | 8/2002 | Hoffman | 250/234 |
| 2002/0135871 A1 | 9/2002 | Vodyanoy et al. | |
| 2003/0030897 A1 | 2/2003 | Suzuki | |
| 2003/0048539 A1 | 3/2003 | Oostman et al. | |
| 2003/0058440 A1 | 3/2003 | Scott et al. | |
| 2004/0047269 A1 * | 3/2004 | Ikenaka et al. | 369/112.08 |
| 2004/0092825 A1 | 5/2004 | Madar et al. | |
| 2004/0195497 A1 * | 10/2004 | Sasaki | 250/234 |
| 2004/0213134 A1 * | 10/2004 | Takada et al. | 369/112.08 |
| 2004/0252379 A1 | 12/2004 | Weiss | |
| 2005/0006573 A1 * | 1/2005 | Dollmann et al. | 250/234 |
| 2005/0057727 A1 | 3/2005 | Troyer | |
| 2005/0078363 A1 * | 4/2005 | Gugel | 359/385 |
| 2005/0104008 A1 | 5/2005 | Oostman et al. | |
| 2005/0219553 A1 | 10/2005 | Kelly et al. | |
| 2005/0224692 A1 | 10/2005 | Tsuchiya et al. | |
| 2006/0061680 A1 | 3/2006 | Madhavan et al. | |
| 2006/0120250 A1 | 6/2006 | Awamura et al. | |
| 2006/0139634 A1 | 6/2006 | Scott et al. | |
| 2006/0187542 A1 | 8/2006 | Westphal et al. | |
| 2006/0197032 A9 | 9/2006 | Oostman et al. | |
| 2007/0064202 A1 * | 3/2007 | Moffat et al. | 353/94 |
| 2007/0102620 A1 | 5/2007 | Bublitz et al. | |
| 2007/0211460 A1 | 9/2007 | Ravkin | |
| 2009/0040754 A1 * | 2/2009 | Brukilacchio et al. | 362/228 |
| 2009/0073553 A1 * | 3/2009 | Hirata | 359/383 |

OTHER PUBLICATIONS

International Search Report dated Feb. 21, 2007 of international application PCT/EP 2006/010745 on which this application is based.
Search Report dated Oct. 26, 2006 of the German Patent Office for German patent application 10 2005 054 184.4 from which this application claims priority.

* cited by examiner

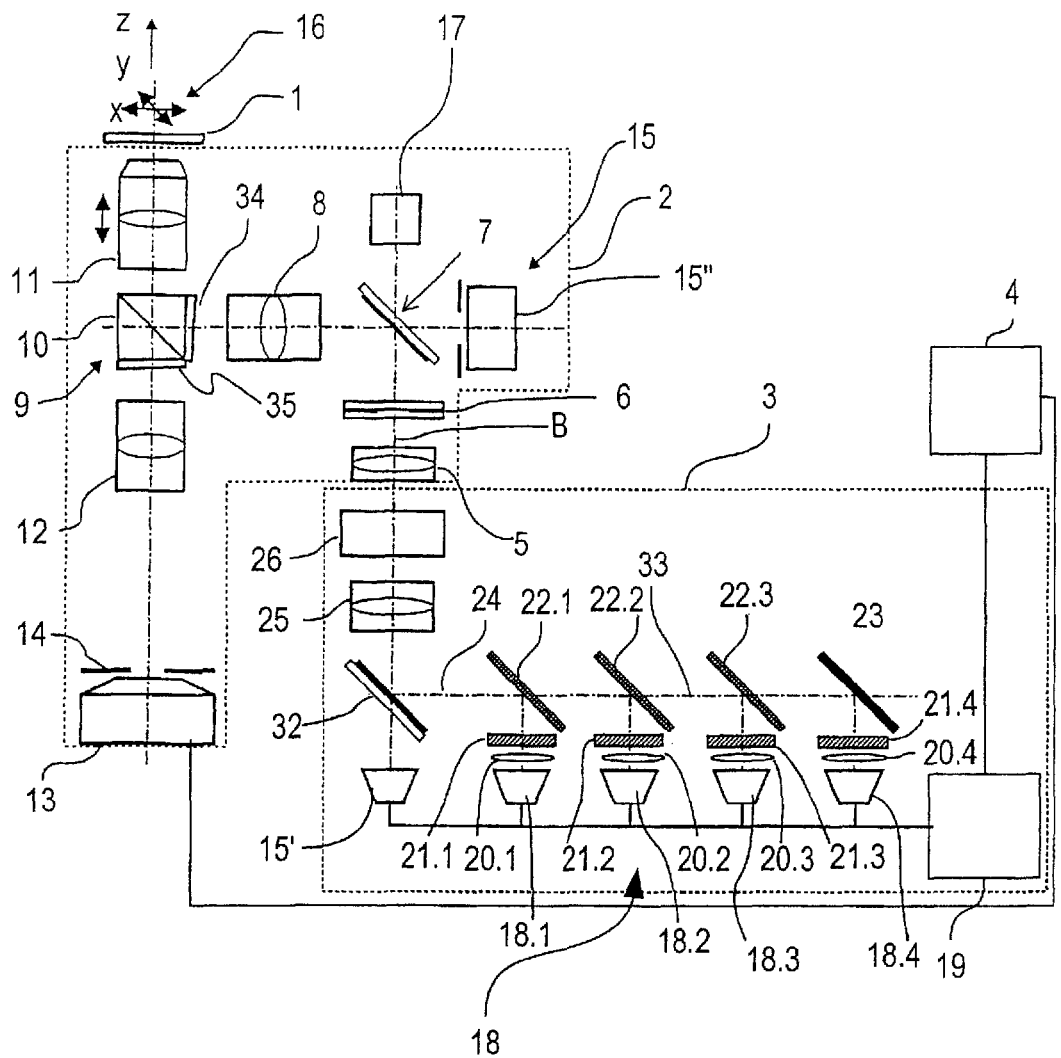
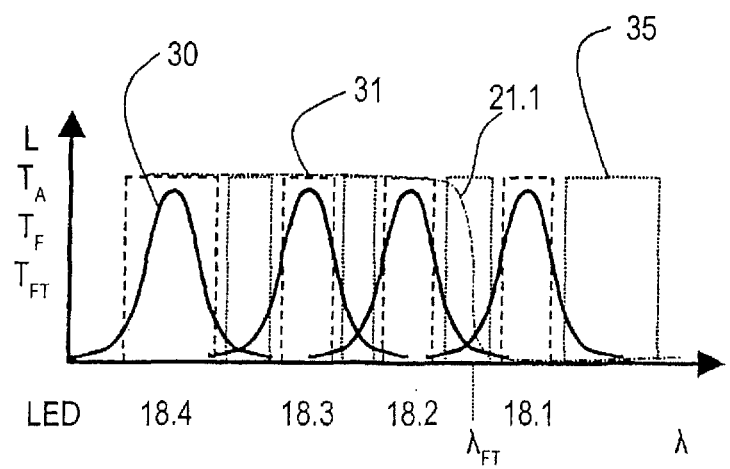
Fig. 1
Fig. 2

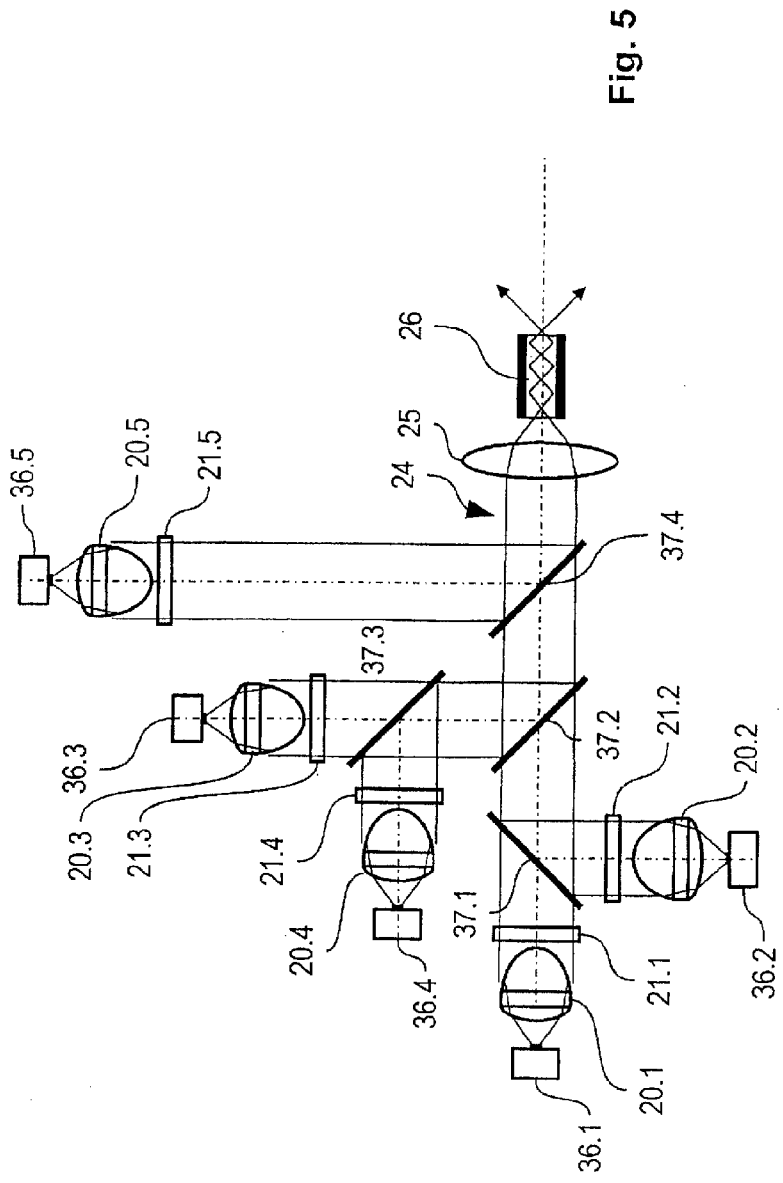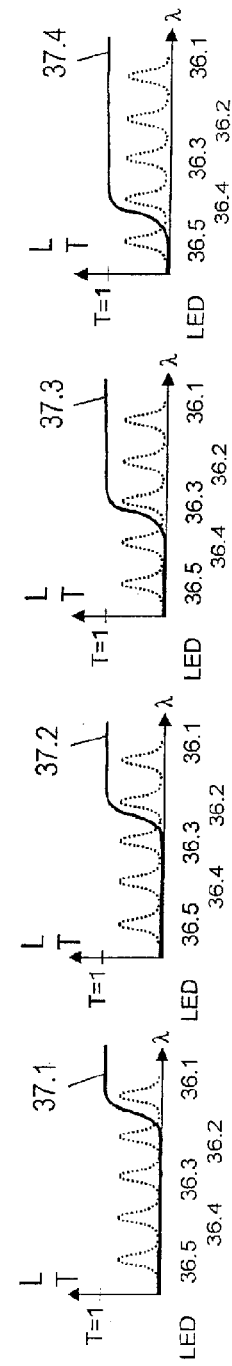

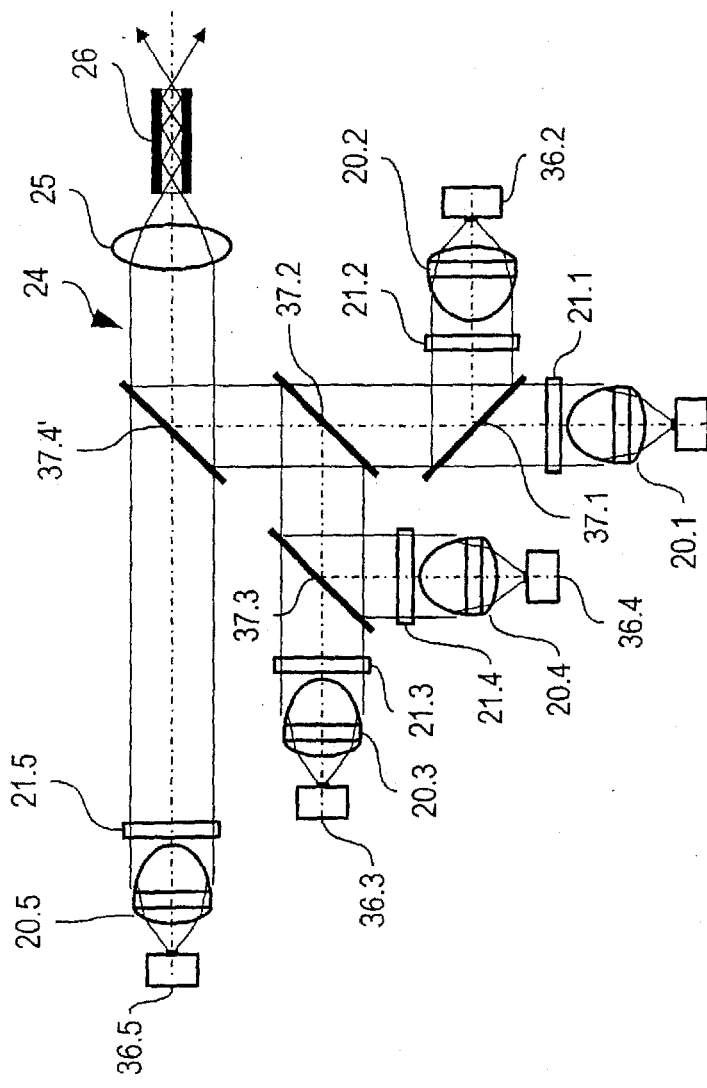
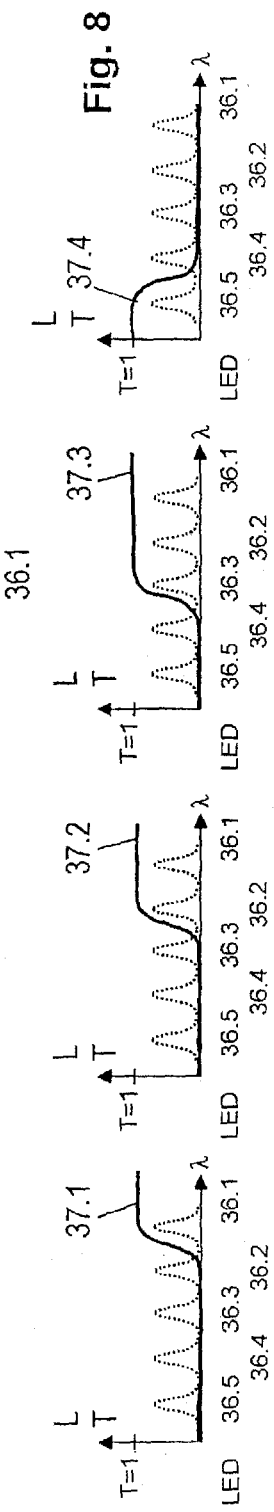
Fig. 7
Fig. 8

MULTISPECTRAL ILLUMINATION DEVICE

CROSS REFERENCE TO RELATED APPLICATIONS

This is a continuation application of application Ser. No. 13/324,472, filed Dec. 13, 2011, which is, in turn, a continuation application of U.S. patent application Ser. No. 12/083, 980, filed Apr. 23, 2008 (now U.S. Pat. No. 8,097,865), which is the national stage of PCT/EP 2006/010745, filed Nov. 9, 2006, designating the United States and claiming priority from German patent application no. 10 2005 054 184.4, filed Nov. 14, 2005, the entire contents of which are incorporated herein by reference.

FIELD OF THE INVENTION

The present invention relates to a multispectral illuminating arrangement as well as optical units, especially, imaging units, examining units, observing units and projection units having such an illuminating arrangement.

BACKGROUND OF THE INVENTION

An important area of use of illuminating units is imaging units and examining units which are provided for the purpose of generating images of an object or a specimen to be examined. Typical examples for such imaging units are microscopes and especially microscopes having a wide field optic which images a pregiven region of the specimen, which is to be imaged or examined, and not only a small point-shaped region of the specimen, onto an image plane. The fluorescence examination has a special role for the optical examination of specimens. Here, the specimen is irradiated with excitation radiation having a suitable excitation spectrum which is selected in dependence upon one or several fluorescence colorants. If these fluorescence colorants are in the specimen, then they interact with the excitation radiation and emit fluorescence radiation which is characteristic for the fluorescence colorant. In this way, a detection of the fluorescence colorants in a specimen is possible. Not only can the presence of the fluorescence colorants be determined but also their concentration can be determined.

An important area of application of fluorescence examinations is molecular biology. Here, fluorescence colorants are used which specifically bond to pregiven substances in a biological specimen and can then be detected in the bonded state. A conclusion as to the presence and the concentration of the pregiven substance in the specimen is possible. For such examinations, so-called fluorescence readers are used which are designed for examining biochips having several regions (mostly even very many regions) delimited from each other with respectively different chemical compositions.

In lieu of fluorescence colorants, also nanoparticles, for example, quantum dots, can be used which fluoresce at at least one wavelength.

Two basic problems occur in such fluorescence examinations. First, the fluorescence intensities are often very low so that influences of other optical radiation in adjacent wavelength ranges or other origins on the detection of fluorescence radiation should be reduced as much as possible in order to obtain a favorable signal-to-noise ratio. For this purpose, illuminating devices are typically used which output excitation radiation with an only very narrow excitation spectrum. On the other hand, emission filters are placed in the detection beam path for the fluorescence radiation from the specimen to a detector. The emission filters preferably pass only radiation in the wavelength range of the fluorescence radiation.

Secondly, for a pregiven fluorescence colorant, the spectrum of the radiation with which the fluorescence of the colorant is excitable as well as also the fluorescence spectrum are specific so that different combinations of excitation radiation and emission filters are necessary for the detection of different fluorescence colorants.

Accordingly, it would be desirable for the rapid examination of specimens as to different fluorescence colorants to have an imaging and examining arrangement which permits a change between the different excitation spectra and/or emission spectra.

For this purpose, a filter wheel having different emission filters can, for example, be used in lieu of a fixed emission filter in the detector beam path. Each one of the emission filters is provided for a pregiven fluorescence spectrum. A white light source can especially be used as an illumination source. This solution has, inter alia, the disadvantage that, on the one hand, only a sequential examination of a specimen as to several fluorescence colorants can be carried out and, on the other hand, mechanical parts must be moved for a change between the examinations.

Additionally or alternatively, a multispectral illumination device can be used with which sequentially and/or parallelly optical radiation can be outputted in at least two different wavelength ranges. Optical radiation in at least two different wavelength ranges is understood to be radiation having an intensity with a pronounced maximum in the wavelength ranges. The intensity must not necessarily vanish in the region between the two wavelength ranges.

In United States patent application publication US 2006/0187542, a device for illuminating objects with light at different wavelengths is described for microscopes, automatic microscopes and apparatus for fluorescence microscopic applications. This device includes LED light sources for object illumination which are arranged in the illuminating beam path of the microscope or apparatus. For moving at least one of the luminescent diodes into an illuminating beam path, a mounting device, which is rotatable about a rotational axis, is provided and has holders for at least one of the luminescent diodes. The mounting device is adjustable via a drive unit so that the luminescent diode can be moved with the centroid wavelength into the illuminating beam path with the centroid wavelength being needed for the particular measurements and/or observations.

This solution too is disadvantageous in that mechanically movable parts are needed and only a sequential examination is possible.

The use of mechanically movable parts has several disadvantages. Thus, the change from the detection of one fluorescent colorant to another takes a certain time which delays the examination of specimens. Furthermore, the assembly is complicated and subjected to wear. Finally, it is very complex to satisfy the required accuracy conditions for the adjustment of the filters or the light sources to the detection beam path or illumination beam path.

In U.S. Pat. No. 6,372,485 and United States patent application publication US 2005/0224692 A1, illuminating devices having three LEDs are described. The radiation of these luminescent diodes is coupled into the same illuminating beam path. The described devices have, however, the disadvantage that the power of the luminescent radiation in the desired wavelength range is not very high compared to the radiation power of the luminescent diodes. Furthermore, the not so compact configuration does not allow a high light-conductance value. Furthermore, with three LEDs, no adequate spectral range for the excitation of fluorescence radiation can be covered.

SUMMARY OF THE INVENTION

The present invention is therefore based on the object of providing an illuminating device for outputting optical radiation having pregiven selectable spectra with the illuminating device being easily assembled and having only slight losses with respect to radiation power.

The object is solved with an illuminating device having at least four semiconductor radiation sources for outputting optical radiation at respectively different emission wavelength ranges. At least three of the semiconductor radiation sources are each assigned at least one color splitter which is reflective for optical radiation of the corresponding semiconductor radiation source. The semiconductor radiation sources and the color splitters are so arranged that the optical radiation, which is emitted by each of the semiconductor radiation sources, is coupled into a common illuminating beam path section. A collimation unit is mounted in each of the beam path sections from the semiconductor radiation sources to the color splitters. Each of the collimator units collimates the radiation outputted by the corresponding semiconductor radiation source.

The illuminating device according to the invention therefore has no movable parts by means of which, to switch over between wavelength ranges, one of the semiconductor radiation sources or a deflection element for optical radiation emitted by these radiation sources must be moved. Rather, only at least four semiconductor sources are provided in combination with at least three corresponding color splitters in order to selectively generate optical illuminating radiation having a pregiven spectrum.

The semiconductor radiation sources can be any desired semiconductor component element emitting optical radiation. For example, laser diodes or superluminescence diodes can be used. Preferably, however, light emitting diodes or luminescent diodes are used. Especially preferred are high power luminescent diodes which radiate optical radiation of high intensity. Preferably, high power color luminescence diodes are used for the illumination source. In order to cover pregiven wavelength ranges, also luminescent diodes with applied luminescent substances for color conversion can be used. These luminescent diodes output optical radiation in a different wavelength range when excited by optical radiation outputted by the semiconductor material of the luminescent diodes.

The luminescent diodes can be especially those having a planar surface from where the optical radiation emanates or luminescent diodes having a transparent dome for reducing refraction index discontinuities to the semiconductor material. The transparent domes are arranged over the surface.

The semiconductor radiation sources are configured for outputting optical radiation in respectively different emission wavelength ranges, that is, they exhibit respectively different emission wavelength ranges or emission spectra. This means that the characteristic wavelengths of the respective emission spectra (for example, intensity maxima of the respective emission spectra or centroid wavelengths of the respective emission spectra or their dominant wavelengths) are spaced from each other, preferably by more than 50 nm. Specifically, the emission peaks of the semiconductor radiation sources preferably do not overlap at least within the half wave width of the peaks, or only in the flanks of the emission peaks. The use of four semiconductor radiation sources permits a good covering of a given spectral range, especially of the total optical spectrum, especially of the visible spectrum as well as the UV range and NIR range. Preferably, at least one of the semiconductor radiation sources is, for this purpose, a UV radiation source or an NIR radiation source having a characteristic emission wavelength in the UV range or NIR range.

In order to make available a radiation power in a particular emission wavelength range, which is adequate for a particular application, it is also possible to use a corresponding field of like semiconductor radiation sources in lieu of only one semiconductor radiation source for a given emission wave region. For example, a field of like luminescent diodes can be used.

The optical radiation which is emitted by each of the semiconductor radiation sources is coupled into a common illuminating beam path section and color splitters are used for this purpose. A color splitter is understood to be every optical element which is transmissive in a pregiven wavelength range and is reflective in other pregiven wavelength ranges. In the illumination arrangement, respective color splitters are assigned to at least three of the at least four semiconductor radiation sources. For the optical radiation of the respective semiconductor radiation sources, the color splitters are either mostly (preferably essentially) reflective or mostly (preferably essentially) transmissive in the region of the emission wavelength range, especially of the characteristic emission wavelength range. With a corresponding switching in and switching out of the semiconductor radiation sources, optical radiation corresponding to the emission wavelengths of the respective switched in semiconductor radiation sources can be outputted as illuminating radiation along the common illuminating beam path section. In this way, a change of the semiconductor sources via mechanical movement in an illuminating beam path is not necessary and this has several advantages. A rapid change is possible between different emission wavelength ranges. Furthermore, the configuration of the device is very simple and of low wear.

Compared to conventional light sources such as arc lamps or halogen lamps, the use of semiconductor radiation sources, especially luminescent diodes, has furthermore the advantage that they have a significantly longer service life. Furthermore, the thermal development by semiconductor radiation sources is significantly less during their operation than in arc lamps or halogen lamps. An active cooling of the semiconductor radiation sources is therefore unnecessary and a passive cooling can be clearly simplified compared to the use of arc lamps or halogen lamps.

A collimating device is mounted in each of the beam path sections between the corresponding ones of the semiconductor radiation sources and the color splitters. The collimating devices collect or more precisely essentially collimate the optical radiation of the respective semiconductor radiation sources. In this way, a very large portion, preferably more than 90%, of the optical radiation, which is emitted by the semiconductor radiation sources, can be directed onto the color splitters so that, overall, a very high efficiency of the semiconductor radiation sources in the illuminating device can be achieved. The collimation furthermore has the advantage that the at least quasi-parallel ray bundle, which arises with the collimation, permits the use of interference filters which permit an especially precise filtering. Also, the function of the color splitters is, as a rule, better with the use of collimated radiation than with the use of uncollimated radiation.

Overall, such an illumination device is generated which not only provides a very simple and low wear configuration because of the omission of parts which have to be moved mechanically, but also outputs a very high illuminating radiation power referred to the radiation power of the semiconductor radiation sources.

A possible application is the spectral separation in multicolor fluorescence. Here, it can be advantageously utilized that specific colorants can hardly be excited and others, in contrast, can be maximally excited via switching in and switching out individual semiconductor radiation sources. Based on several such measurements, the quantity ratio of the colorants can be determined mathematically.

Furthermore, also a pixel shift can be avoided which often arises because of a mechanical filter exchange. The radiation load on the specimen can be minimized by the rapid switchability of the semiconductor radiation sources. A mechanical shutter for the illumination is no longer needed.

The illumination source is suitable for all types of microscopes. The following, for example, belong to these types of microscopes: universal microscopes, optical readers (inter alia, biochip readers, titer-plate readers), stereo microscopes, surgical microscopes and ophthalmologic apparatus.

Preferably, the illuminating device includes a control unit by means of which the semiconductor radiation sources can be switched on and off independently of each other. This embodiment affords the advantage that a selection is easily possible between different emission wavelength ranges of the illuminating radiation outputted by the common illuminating beam path section. The control unit can, for this purpose, include operator-controlled elements such as switches which are to be operated by the user. Preferably, however, a control input is provided via which the control unit can receive control signals in response to which the control unit switches one or several of the semiconductor radiation sources on and off. The semiconductor radiation sources can be switched on and off individually or also in combination with each other. This embodiment permits an especially rapid change between different emission wavelength ranges and, with a combination of several emission wavelength ranges, a simultaneous illumination with radiation in different emission wavelengths and therefore a simultaneous detection of several fluorescence colorants in a specimen when the emission wavelength ranges of the semiconductor radiation sources and the color splitters are correspondingly selected.

Here, it is especially advantageous that the control unit is so configured that the emission radiation powers of the semiconductor radiation sources can be adjusted independently of each other. This embodiment affords the advantage that the radiation powers of the individual semiconductor radiation sources can be precisely adjusted in contrast to arc lamps and halogen lamps without a change of the color spectrum. It is especially possible to so adjust the radiation powers that the optical radiation, which is emitted by the semiconductor radiation sources into the common illuminating beam path section, has respectively the same emission radiation power.

Basically, different numbers of semiconductor radiation sources can be used. Preferably, the radiation device, however, has a total of five to eight semiconductor radiation sources having respective emission wavelength ranges. Corresponding color splitters are assigned to at least four to seven of these semiconductor radiation sources and the emission radiation of the semiconductor radiation sources is coupled into the common illuminating beam path section via the respective color splitters. In this way, an especially good coverage of a given spectral range is possible, especially of the total optical spectrum.

The beam paths from the semiconductor radiation sources to the last color splitter in the illuminating beam path of the illuminating device ahead of the common illuminating beam path section can run in different ways. For an especially compact form of the illuminating device, the beam paths from the semiconductor radiation sources up to directly behind the last color splitter ahead of the common illuminating beam path section form preferably a binary tree. As in graph theory, a binary tree is understood to be a tree having a root and, extending from the root, branches, several knots connected to the root via the branches and, at the free ends of the branches, which extend from the knots or root, there are leaves wherein each knot is connected to at most two other knots. Such a binary tree therefore has $2^N$ leaves for $2^N-1$ knots and these leaves are given by the semiconductor radiation sources in the illuminating device. N identifies a natural number greater than 1. The knots and the root correspond respectively to the color splitters while the semiconductor radiation sources define the leaves. The illuminating device therefore contains $2^N$ semiconductor radiation sources having respectively different emission wavelength ranges and at least $2^N-1$ corresponding color splitters. This embodiment affords the advantage that the illuminating device can have an especially compact configuration.

The collimation units can be configured to be the same or respectively different. Especially, concentrators or holographic or diffractive elements can be used which permit a collimation of the optical radiation outputted by corresponding ones of the semiconductor radiation sources. Preferably, however, at least one of the collimating units includes an aspheric lens or an aspheric mirror. This embodiment of the collimator unit affords the advantage that the aspheric configuration permits an especially good bundling of the optical radiation outputted by the respective semiconductor radiation source and thereby radiation losses via less directed radiation of the optical radiation from the semiconductor radiation sources can be reduced.

In order to make available the illuminating radiation with as narrow as possible and sharply defined spectra, it is preferable that in at least one radiation beam section from one of the semiconductor radiation sources to one of the color splitters, at least one bandpass filter is mounted preferably between the collimating unit which is mounted in the beam path section and the color splitter. The bandpass filter functions to mask long spectral extensions of the emissions spectra of the semiconductor radiation sources and thereby possibly avoid disturbing background signals. This affords the advantage that a later multispectral evaluation is facilitated, for example, for a fluorescence examination. The bandpass filter preferably has a spectral width of less than 100 nm.

Semiconductor radiation sources are up to now not available for any desired emission wavelength ranges at economical cost. It is therefore preferred that the illuminating device includes at least one semiconductor radiation source having at least one luminescence substance for color conversion. A bandpass filter is mounted in the beam path of the semiconductor radiation source and is coupled likewise into the common illuminating beam path section. The bandpass filter is disposed preferably between a collimating unit assigned to the semiconductor radiation source and the semiconductor radiation source itself. A color conversion via a luminescence substance is understood to be that the luminescence substance converts radiation, which is outputted from a radiation emitting layer of the semiconductor radiation source, into radiation of the desired wavelength range via fluorescence and/or phosphorescence, that is, radiation of another color. The bandpass filter is so selected that the radiation of the semiconductor radiation source is spectrally limited to a suitable wavelength range. Preferably, that range lies in the region of 570 nm. This embodiment affords the advantage that gaps in the wavelength range of the optical spectrum, which is covered by the semiconductor radiation sources, can be filled in that a corresponding bandpass filter is used.

Basically, any number of color splitters can be used which permit an in-coupling of optical radiation into respective emission wavelength ranges of the semiconductor radiation sources into the common illuminating beam path section. Preferably, three color splitters are mounted in one and the same beam path section of the illuminating device and have filter edges at wavelengths which rise or fall along the beam path section. The semiconductor radiation sources whose emission radiation passes through these color splitters then exhibit emission wavelength ranges whose characteristic emission wavelength rises and falls monotonically in the corresponding sequence. As color splitters especially those can be used which have a spectral transmission capability in step form (that is, step filters) or band form. The wavelengths at which the steps occur can then monotonically rise or fall. This selection of color splitters affords the advantage that a successive in-coupling of the optical radiation can take place with respectively different emission wavelength ranges with only slight losses.

Preferably, a homogenizing unit is mounted in the common illuminating beam path section downstream of the color splitters. The homogenizing unit functions to homogenize the intensity distribution of the optical radiation, which is outputted by one or several of the semiconductor radiation sources, over the cross section of the resulting illuminating beam. The homogenization unit affords the advantage that a uniform illumination of the specimen is easily possible. As a homogenizing unit, especially transparent or hollow rods having reflecting side walls can be used as can diffractive optical elements or scatter plate discs. The use of rods or hollow rods having reflective walls affords the advantage that the losses therein are especially low.

Preferably, the light conductance values of the semiconductor radiation sources and the downstream optical elements of the illuminating device are adapted to each other for maximizing the energy flow of the radiation to be emitted. In this way, especially losses can be minimized which are caused by the geometric arrangement of the semiconductor radiation sources and the optical elements so that illuminating radiation having a high intensity relative to the radiation power of the semiconductor component elements can be achieved.

The illuminating device does not necessarily have to be used to generate optical radiation in only one of the emission wavelength ranges. Thus, in a preferred embodiment, the control unit is configured to drive at least two of the semiconductor radiation sources to generate white light of variable color temperature via additive color mixing of the optical radiation emitted by the at least two semiconductor radiation sources. This embodiment affords the advantage that light of a pregiven color temperature can easily be generated.

The illuminating device is suitable generally for illuminating purposes which require a rapid variation of the color spectrum. The subject matter of the invention is therefore especially also an optical arrangement having an illuminating device according to the invention. In addition to the illuminating device, the optical arrangement includes at least one further optical component which is mounted in the beam path of the radiation outputted by the illuminating device.

Especially, the illuminating device can preferably be used for digital projection systems. In this case, an especially wide color range is covered. The subject matter of the invention is therefore also an optical arrangement for projection of color images and/or films having an illuminating device according to the invention. This can especially have a projection optic arranged in the beam path of the radiation emitted by the illuminating device.

The illuminating device is especially preferred, however, for examining specimens. The subject matter of the present invention is therefore an optical arrangement for examining a specimen, especially, a wide field microscope or a fluorescence reader having an illuminating device according to the invention. Such an examining arrangement is characterized in that it has only few or no movable parts caused by the configuration of the illuminating device and is therefore cost effective and simple to manufacture. Furthermore, the examining arrangement can be very compactly configured.

Preferably, the arrangement is configured for carrying out fluorescence examinations on a specimen and, for this purpose, has at least one multiband emission filter or multiband emission filter set in a detection beam path for fluorescence radiation emanating from the specimen. In the following, and for the sake of simplicity, a multiband emission filter set is also identified as a multiband emission filter. The multiband emission filter can function especially as an emission filter for generated fluorescence radiation. Arrangements built up in this manner for carrying out fluorescence examinations have significant advantages compared to known fluorescence examining arrangements especially when the semiconductor radiation sources can also be driven simultaneously. Accordingly, in a combined operation of at least two of the semiconductor radiation sources, a simultaneous detection of several fluorescence colorants in the specimen is possible which significantly accelerates the examination of specimens especially in sequential examinations. Furthermore, an exchange of the emission filters and an image offset occurring possibly as a consequence thereof can be easily avoided via the switchover of two different semiconductor radiation sources. The image offset arises because of mechanical filter exchange. Furthermore, the radiation load on a specimen can be reduced during the examination because of the rapid switchover between the different semiconductor radiation sources. The multiband emission filter is preferably so configured that, in combination with a corresponding selection of the excitation spectra or emission spectra of the illuminating device, fluorescence examinations of at least two, preferably three to four, fluorescence substances of a specimen are possible. For this purpose, especially the excitation spectra are to be matched to the fluorescence colorants.

To obtain an especially high signal-to-noise ratio, the device includes preferably a multiband excitation filter in the illuminating beam path. The excitation spectra can be very sharply defined because of this multiband excitation filter. Furthermore, a multiband color splitter is provided by means of which the illuminating radiation or excitation radiation, which is outputted by the illuminating device, can be coupled into the illuminating beam path and/or imaging beam path of the examining arrangement. This embodiment likewise affords the advantage that an especially good signal-to-noise ratio is obtained because the multiband color splitter also operates as a filter. The bands are preferably adapted to the excitation spectra and fluorescence spectra of the fluorescence colorants utilized.

In an especially preferred embodiment, the multiband emission filter is contained in a filter cube which further has a multiband filter or multiband filter set, which is arranged in the illuminating beam path of the examining device, and a multiband color splitter for deflecting the illuminating radiation of the illuminating device or deflecting fluorescence radiation emanating from the specimen. This affords the advantage that a very compact configuration is obtained and an alignment of the optical elements with respect to each other is simplified.

Preferably, in the fluorescence examining arrangement, at least one of the emission spectra of the illuminating device lies with its characteristic wavelength between two emission wavelength ranges of the multiband emission filter. This affords the advantage that via the excitation radiation (that is, the emission radiation of the semiconductor radiation sources of the illuminating device) little optical radiation can affect the detection of the fluorescence radiation. Preferably, in the arrangement, the centroids of the emission spectra of the illuminating device alternate with the emission wavelength ranges of the emission filters. The characteristic emission wavelength can be especially a wavelength wherein the emission spectrum has a maximum or a centroid wavelength, which results as a medium value of the emission wavelength weighted with the emission intensity, or the dominant wavelength.

Preferably, the device includes at least two multiband filters having filter edges which are shifted relative to each other by a distance of between 10 nm and 90 nm. This embodiment affords the advantage that a greater number of different fluorescence colorants can be used for examination.

It is especially advantageous when the examining arrangement includes a receptacle for at least two filter cubes by means of which one of the filter cubes is movable into a detection beam path of the arrangement. This embodiment affords the advantage that a rapid exchange of the filter cubes is possible which especially can greatly accelerate sequence examinations of specimens, especially, with biochip readers. The receptacle can be configured as a slider, wheel or turret. The movement of the receptacle can be manual or the receptacle can be moved by an electric drive. A correspondingly greater number of semiconductor radiation sources with respectively different emission spectra is not necessarily needed.

As already explained, the examining arrangement can preferably be configured as a microscope especially as a wide field microscope. The microscope can especially also be designed as an inverse microscope.

The subject matter of the invention is also a method for measuring the concentration of a number M of pregiven fluorescence colorants in a specimen wherein M measurements are carried out with a fluorescence examining arrangement, especially, a fluorescence examining arrangement according to the invention. For each of the measurements, another number less or equal to M of emission wavelength ranges, which correspond to the excitation spectra of the fluorescence colorants, are used for forming excitation radiation and the specimen is irradiated with the excitation radiation and the resulting fluorescence radiation is detected. The concentration of the fluorescence colorant is determined from the detection results of the M measurements. M is a natural number. Compared to a method wherein M measurements are sequentially carried out for only one fluorescence colorant in each case, this method affords the advantage that possible excitations of fluorescence radiation by another than the semiconductor radiation source, which is actually provided for the excitation of given fluorescence colorants, can be mathematically eliminated. For the M measurements, especially a successively increasing or decreasing number of emission wavelength ranges or excitation wavelength ranges can be used.

Preferably, however, especially also the following include an illuminating device according to the invention: an optical arrangement for examining the eye, especially a fundus camera, or an optical arrangement for examining and/or viewing tissue, especially a surgical microscope.

BRIEF DESCRIPTION OF THE DRAWINGS

The invention will be explained in greater detail in the following with the reference to the drawings.

FIG. 1 shows a schematic of a fluorescence examining arrangement in the form of a wide field fluorescence microscope according to a first preferred embodiment of the invention having an illuminating device according to a preferred embodiment of the invention;

FIG. 2 is a schematic representation of the emission spectra of the following: the semiconductor radiation sources of the illuminating device in FIG. 1, the transmission performance of the excitation band filters of the illuminating device in FIG. 1 and the transmission performance of the multiband color filters for the fluorescence radiation of the examining arrangement of FIG. 1;

FIG. 5 shows an illuminating arrangement according to a third preferred embodiment of the invention;

FIG. 6 shows a schematic representation of the emission spectra of the semiconductor radiation sources and of the spectral transmission performance of the color splitters of the illuminating device of FIG. 5;

FIG. 7 shows an illuminating device of a fourth preferred embodiment of the invention;

FIG. 8 is a schematic representation of the emission spectra of the semiconductor radiation sources and of the spectral transmission performance of the color splitters of the illuminating device of FIG. 7;

DESCRIPTION OF THE PREFERRED EMBODIMENTS OF THE INVENTION

Figure 3:
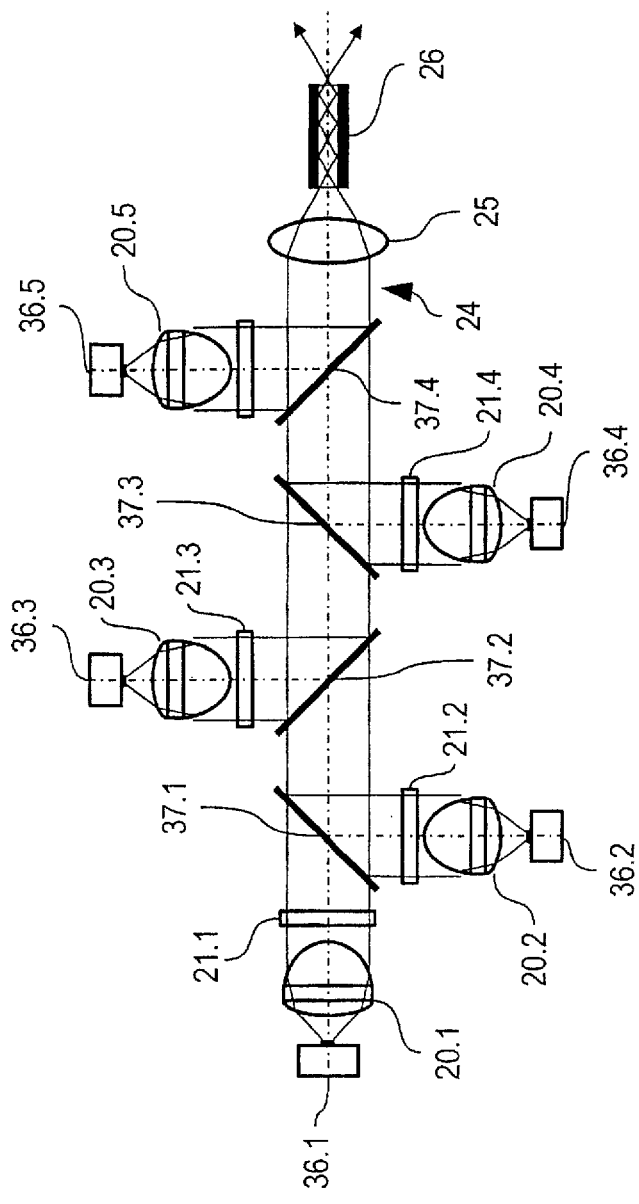
FIG. 3 is an illuminating device according to a second preferred embodiment of the invention.

In FIG. 1, an examining arrangement of a first preferred embodiment of the invention in the form of a fluorescence microscope for examining a specimen 1 includes a microscope part 2, a multispectral illuminating device 3 according to a first preferred embodiment of the invention and a control and evaluation unit 4 for driving the illuminating device 3 and detecting and evaluating images, more precisely fluorescence images, of the specimen 1 generated by the microscope part 2.

The illuminating device 3 supplies illuminating radiation into an illuminating beam path B of the microscope part 2.

The microscope part 2 is configured of a collimating optic 5 for collimating the optical radiation outputted by the illuminating device 3, a field diaphragm 6 mounted downstream of the illuminating device 3, a partially transparent deflecting mirror 7, an illuminating tube 8 having an optic, a filter cube 9 having a multiband color splitter 10 and an objective 11. Illuminating radiation exiting from the illuminating beam path then reaches the specimen 1.

The specimen 1 is imaged by the microscope part 2. The microscope part 2 has for this purpose the objective 11, the filter cube 9 and a detection tube 12 having a detection optic which together form an imaging or detection beam path and image the specimen 1 onto a camera 13 with diaphragm 14. The filter cube 9 has in the imaging beam path a multicolor filter or a multiband color filter 35, which is transmissive for the fluorescence radiation to be detected, but filters out other spectral components, especially excitation radiation. The camera 13 is connected via a signal connection to the control and evaluation unit 4 so that images, which are detected by the camera 13 can be detected by the control and evaluation unit 4.

For focusing the image, the microscope part 2 has an autofocusing device 15 having a white light-emitting diode 15' and an autofocus sensor 15" having a diaphragm. The autofocus device drives a z-drive (not explicitly shown in FIG. 1) for the objective 11 by means of which the objective 11 is displaceable for focusing along the optical axis of the objective 11, that is, in the z-direction. The precise configuration and precise function of the autofocus sensor 15" are described in United States patent application publication US 2007/0102620 whose content is herewith incorporated into the disclosure by reference.

The camera 13 includes a CCD-field for receiving detection radiation and for generating signals which reproduce the energy and therewith gray steps. The energy is received from an element of the CCD-field.

A motor-driven mechanical stage 16 serves for selecting a region of the specimen 1 to be imaged. The mechanical stage 16 is indicated only by two double arrows in FIG. 1. By means of the mechanical stage 16, the specimen 1 is movable in an xy-plane orthogonally to the z-axis. The drive (not shown in FIG. 1) of the mechanical stage 16 is connected via a control connection (likewise not shown) to the control and evaluation unit 4 and is controllable thereby.

In the example, the control and evaluation unit 4 includes a personal computer with conventional input and output apparatus, especially a monitor not shown in FIG. 1. The illuminating device 3 and the microscope part 2 are driveable via a graphical user interface of the control and evaluation unit 4.

A monitor detector 17 is likewise connected to the control and evaluation unit 4. The monitor detector 17 is mounted behind the partially transparent deflecting mirror 7 in the extension of the optical axis of the collimating optic 5. The monitor detector 17 receives a part of the illuminating radiation outputted by the illuminating device 3 and generates signals which reproduce the energy or intensity of the illuminating radiation. This portion of the illuminating radiation is determined by the transmission of the deflecting mirror 7. The control and evaluation unit 4 receives the signals and determines the intensity impinging on the specimen 1 from these signals.

The multispectral illuminating device 3 functions to emit optical radiation in one or several pregiven wavelength ranges corresponding to drive signals from the control and evaluation unit 4.

For this purpose, and in addition to the white light-emitting diode 15', the multispectral illuminating device 3 has several semiconductor radiation sources 18, in the example, four light emitting diodes (18.1, 18.2, 18.3, 18.4) having respectively different emission wavelength ranges, in the example, red, green, blue or ultraviolet. The illuminating device 3 further includes a control unit 19 which is connected to the light emitting diodes for driving or supplying the same with current. The following are mounted downstream of the light diodes (18.1, 18.2, 18.3, 18.4) in corresponding beam path sections: respective collimating units (20.1, 20.2, 20.3, 20.4); excitation band filters (21.1, 21.2, 21.3, 21.4) as well as respective color splitters (22.1, 22.2, 22.3) and a mirror 23. The color splitters (22.1, 22.2, 22.3) couple the radiation of the semiconductor radiation sources (18.1, 18.2, 18.3) successively into a beam path from the semiconductor radiation source 18.4 and therewith finally into a common illuminating beam path section 24.

In the further course of the common illuminating beam path section 24, the following are provided: a partially transparent deflecting mirror 32, an optic 25 and a homogenizing unit 26. The partially transmitting deflecting mirror 32 functions only for the deflection and the coupling-in of the radiation of the light emitting diode 15' of the autofocusing unit 15 into the common illuminating beam path section 24. The homogenizing unit 26 is in the form of a mirrored hollow rod into which the optic 25 couples the light from the common illuminating beam path section 24. The homogenizing unit 26 functions to evenly distribute the intensity of the illuminating radiation in the illuminating beam path section 24 over the beam cross section of the illuminating radiation so that an essentially constant intensity is achieved over the beam cross section.

Figure 12:
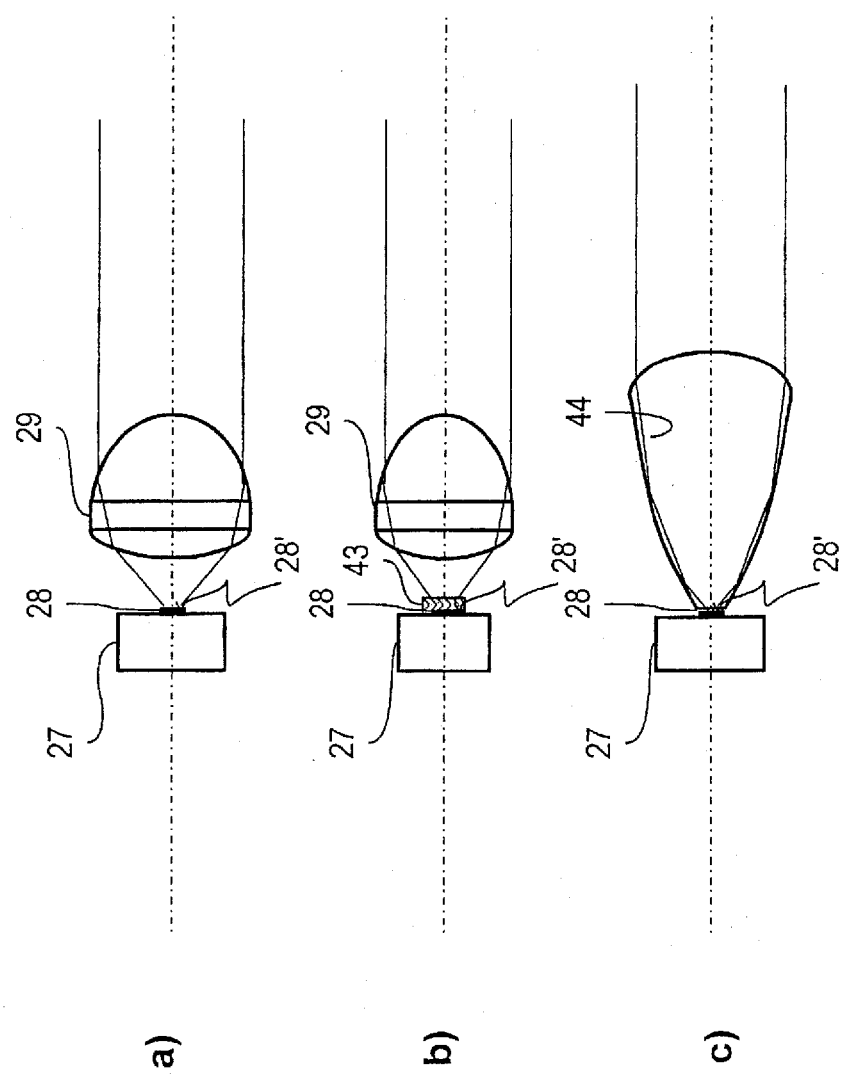
FIGS. 12a, 12b and 12c show a schematic representation of the semiconductor radiation sources and different embodiments of collimator devices arranged ahead thereof for illuminating devices of additional preferred embodiments of the invention; and, FIG. 13 shows a schematic representation of an examining arrangement according to a further preferred embodiment of the invention.

The light emitting diodes 18 each have a carrier and a surface emitting optical radiation. In FIG. 12a, the carrier 27 and the actual light emitting diode chip 28 are shown by way of example for the light emitting diode 18.1. The light emitting diode chip 28 has the radiation emitting surface 28'.

The control unit 19 is so configured that it responds to control signals of the control and evaluation unit 4 to, on the one hand, switch on and switch off the semiconductor radiation sources 18 individually or in combination and, on the other hand, individually controls or adjusts the brightness of the particular switched-on semiconductor radiation source or the intensity of the optical radiation outputted by this source by adjusting the supply voltage. The current supply, which is provided for each of the semiconductor radiation sources, has preferably switching times in the submillisecond range, that is, faster than approximately 1 ms so that a rapid switching on and switching off of each of the semiconductor radiation sources is possible.

The collimating units 20.1 to 20.4 are arranged in the beam path of corresponding ones of the semiconductor radiation sources 18.1 to 18.4. The collimating units 20.1 to 20.4 collimate the optical radiation outputted by the semiconductor radiation sources. In the example, aspheric lenses 29 of high numerical aperture, preferably greater than 0.5, are used as collimating units, as shown in FIG. 12a. Spherical lenses could, in principle, also be used, but the aspheric lenses 29 have better collimating characteristics. The collimating units 20 and the optic 25 are so designed and arranged that a component as large as possible is coupled into the homogenizing unit 26 from each of the semiconductor radiation sources. Especially, the collimating units and the optic 25 are so designed in the common illuminating beam path section 24 forward of the homogenizing unit 26 that the light-conductance values are optimally adapted to each other. The optic, which is formed by the collimating unit and the in-coupling optic 25 for the homogenizing unit 26, is telecentrically designed so that the pupil of the collimating unit 20 and the pupil of the in-coupling optic 25 are superposed.

The optic 25 has a focal length corresponding to the necessary imaging scale and focuses the optical radiation for this purpose into the input surface of the homogenizing unit 26. The distances of the semiconductor radiation sources 18 to the collimating unit 26 are in each case different in the present example. For this reason, the collimating units (in the example, the aspheric lenses 29) are specifically adapted in configuration and/or arrangement for each of the semiconductor radiation sources 18. In this example, like aspheric lenses are used whose position between the particular light emitting diode chip and the color splitter or mirror is correspondingly optimized. The color splitter or mirror follows the light emitting diode in the beam path. In an alternate embodiment, specifically adapted aspherical lenses can be used as collimating units for each of the semiconductor radiation sources in correspondence to their position in the beam path.

As already mentioned, the semiconductor radiation sources (18.1, 18.2, 18.3, 18.4) emit optical radiation with respectively different emission spectra which are shown schematically in FIG. 2. In FIG. 2, in the same diagram, the following are shown qualitatively as a function of the wavelength λ: the emission radiation power L of the semiconductor radiation sources 18 (solid line); the transmission $T_A$ of the excitation band filters 21.1 to 21.4 (broken lines); the transmission $T_F$ of the multicolor filter 35 (dotted line); and, the transmission $T_{FT}$ of the color splitter 22.1. The respective emission spectra 30.1 to 30.4 of the semiconductor radiation sources 18.1 to 18.4 each have a peak. The characteristic emission wavelength of the particular emission spectrum is in this embodiment, as in the following embodiments, the wavelength having the maximum emission intensity. In another variation, the centroid wavelength (that is, the mean value of the emission wavelengths weighted by the emission intensity) can be used as characteristic emission wavelength. The luminescent diodes 18.1 to 18.4 therefore emit, expressed by the color of the characteristic emission wavelength, optical radiation in spectra having decreasing characteristic wavelength: the light emitting diode 18.1 in red, the light emitting diode 18.2 in green, the light emitting diode 18.3 in blue and the light emitting diode 18.4 in ultraviolet. The light emitting diodes are so selected that the emission spectra are well suited for exciting at least four pregiven fluorescence colorants distributed over the optical spectrum from UV up to red light.

The excitation band filters 21.1 to 21.4, which are configured as interference filters, having transmission bands 31.1 to 31.4 narrow the spectral width of the emission spectra 30.1 to 30.4 and so prevent a cross talk for different simultaneous fluorescence examinations for different fluorescence colorants. The transmission bands 31.1 to 31.4 are adapted to the respective emission spectra of the semiconductor radiation sources.

While the mirror 23 functions only for the deflection of the radiation, which is outputted by the light emitting diode 18.4, and therefore only has a highest possible reflection capacity in the region of the emission spectrum of the light emitting diode 18.4, the color splitters 22.1 to 22.3 have a transmission selected in correspondence to the arrangement in the beam path and the arrangement of the light emitting diodes. The color splitters 22.1 to 22.3 are assigned to corresponding ones of the semiconductor radiation sources 18.1 to 18.3. The color splitters 22.1 to 22.3 have a step-shaped transmission capacity in the wavelength range covered by the emission spectra of the light emitting diodes 18.1 to 18.4. With this transmission capacity, the transmission for wavelengths below a flank wavelength $\lambda_{FT}$ is very high, whereas, above the flank wavelength $\lambda_{FT}$, the reflection is very high, ideally almost 100%. The flank wavelength $\lambda_{FT}$ shows the position of the step. This form is shown schematically in FIG. 2 for the color splitter 22.1.

Along the beam path from the mirror 23 or the semiconductor radiation source 18.4 to the homogenizing unit 26, the other semiconductor radiation sources 18.1 to 18.3 are therefore arranged in a sequence of decreasing characteristic emission wavelengths and the color splitters 22.1 to 22.3, which are assigned thereto, are arranged in a corresponding sequence of monotone decreasing flank wavelengths.

The flank wavelengths are so selected that optical radiation from a semiconductor radiation source, which is assigned to the corresponding color splitter, is reflected and is thereby coupled into the beam path 33 from the semiconductor radiation source 18.4 with the lowest characteristic emission wavelength to the homogenizing unit 26, but passes the radiation of the other light emitting diodes whose radiation is already coupled into the beam path 33 in the direction of the semiconductor radiation source of greatest characteristic emission wavelength. The flank wavelengths are especially so selected that they lie in the center between the characteristic emission wavelengths of the semiconductor radiation sources 18.

The optical excitation radiation, which is emitted by the illuminating device 3, is coupled into the illuminating tube 8 by the deflecting mirror 7 after passing the collimating optic 5 and the field diaphragm 6. Excitation radiation exiting from the illuminating tube 8 then reaches the filter cube 9 which includes a multiband excitation filter 34 ahead of the multiband color splitter 10. The multiband excitation filter 34 filters out components in unwanted wavelength ranges which are possibly still contained in the excitation radiation. In a variation of the embodiment, and when utilizing a so-called Pinkel filter set, the filter 34 is not needed. A Pinkel filter set is a filter set, which is suggested by Professor Dan Pinkel, which, for example, can be used for FISH microscopy (fluorescence-in-situ-hybridizing microscopy).

The multiband color splitter 10 is at least partially reflective for the excitation radiation. After deflection by the multiband color splitter 10, the excitation radiation is focused on the specimen 1 by the objective 11 and there excites fluorescence radiation characteristic for the particular fluorescence colorant when corresponding fluorescence colorants are present.

The detection radiation emanating from the specimen 1, which especially includes the excited fluorescence radiation, is parallelized by the objective 11 and reaches the multiband color splitter 10 which is so designed that optical radiation in the wavelength ranges, in which the fluorescence radiation of the given fluorescence colorants lies, is passed but that other radiation is deflected. The passed detection radiation is then again filtered by the multicolor filter or emission filter 35, which is transmissive in narrow wavelength ranges about the wavelengths of the expected fluorescence radiation emanating from the pregiven fluorescence colorants, but not for radiation having wavelengths between these ranges. The transmission of one such multicolor filter 35, which is matched to the illuminating device 3, is exemplary and shown schematically in FIG. 2 by a dotted line.

The remaining radiation is imaged by the detection optic in the detector tube 12 onto the camera 13 having diaphragm 14 where the occurring image is detected. The occurring detection signals are then detected by the control and evaluation unit 4 whereby, overall, an image of the distribution and concentration of the pregiven colorant substances is detected in the specimen 1.

To generate the images, the semiconductor radiation sources 18 can be switched on sequentially or in combination. The intensity of the particular outputted optical radiation can be controlled by the control unit 19. This is especially advantageous when an ocular is used for the direct viewing in lieu of the camera 13.

The following four preferred embodiments of an examining arrangement according to the invention differ from the examining arrangement of the first embodiment by the configuration of the illuminating device 3. In lieu of the illuminating device 3, other preferred embodiments of illuminating devices according to the invention are used. The autofocusing unit is dispensed with. All other parts are unchanged except for matching to the changed illuminating device so that the description with respect to the first embodiment also applies here. Also, in the illuminating device, for some components, which correspond to the first embodiment, the same reference characters are used.

In the FIGS., the control unit for the semiconductor radiation sources is not shown in each case. The control unit is different from the first embodiment only in that the control unit is configured for driving five semiconductor radiation sources. The drive of the individual semiconductor radiation sources can be as in the first embodiment.

What was said for the first embodiment with respect to the configuration and arrangement of the collimating units 20, the in-coupling optic 25 and the homogenizing unit also applies here.

The illuminating devices each have five semiconductor radiation sources in lieu of four semiconductor radiation sources and the characteristic emission wavelengths of the emission spectra are different and are distributed over the spectral range from the UV to the red end of the visible spectrum. Especially one of the semiconductor radiation sources is a radiation source for optical radiation in the UV range.

The semiconductor radiation sources do not differ between the following embodiments. Accordingly, the semiconductor radiation sources are identified by the same reference numeral 36. The radiation sources can be selected in the form of light emitting diodes as shown below. If the numerals 36.1 to 36.5 identify the respective semiconductor radiation sources in one embodiment, then, for example, the light emitting diode 36.1 can emit radiation having a characteristic emission wavelength in the IR or red region of the optical spectrum; light emitting diode 36.2 can emit radiation having a characteristic emission wavelength in the yellow region of the spectrum; light emitting diode 36.3 can emit radiation having a characteristic emission wavelength in the green region of the spectrum; light emitting diode 36.4 can emit radiation having a characteristic emission wavelength in the blue region of the spectrum; and, light emitting diode 36.5 can emit radiation having a characteristic emission wavelength in the UV range.

In the first of four embodiments, which is shown schematically in FIG. 3, the optical radiations of the semiconductor radiation sources 36.1 to 36.5 are, in the direction from the radiation source 36.1 to the homogenizing unit 26, successively coupled by means of four corresponding color splitters 37.1 to 37.4 into a beam path (which is linear in the example) from the radiation source 36.1 to downstream of the color splitter 37.4. The end of the beam is defined by the common illuminating beam path section 24.

Figure 4:
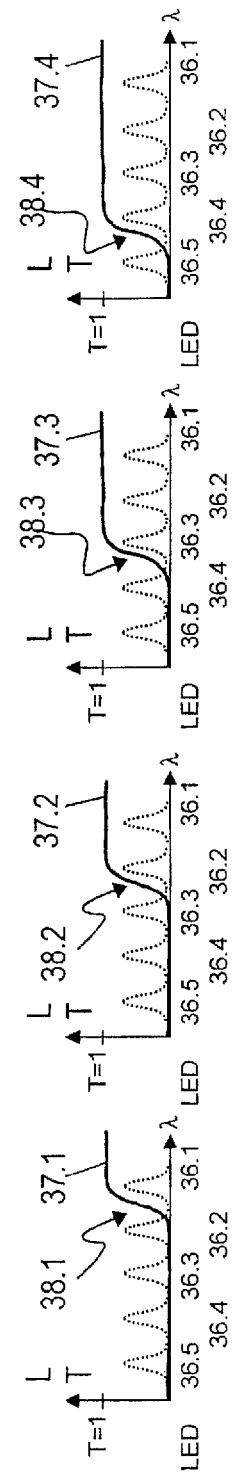
FIG. 4 is a schematic representation of the emission spectra of the semiconductor radiation sources and of the spectral transmission performance of the color splitters of the illuminating device of FIG. 3.

As in the first embodiment, the four color splitters 37.1 to 37.4 have a step-shaped transmission in the optical wavelength range. This is shown in FIG. 4 which shows the respective transmission for each of the four color splitters as a function of the wavelength $\lambda$ as a solid line and shows the emission spectra of the light emitting diodes 36.1 to 36.5, that is, the intensity as a function of the wavelength as broken lines or dotted lines.

While the radiation of the light emitting diode 36.1 is not deflected, the light emitting diodes 36.2 to 36.5 are arranged sequentially along the beam path of the light emitting diode 36.1 in a sequence of decreasing wavelength. The color splitters 37.1 to 37.4 are arranged at 45° relative to the linear beam path emanating from the light emitting diode 36.1 in order to couple the radiation of the light emitting diodes 36.2 to 36.5 into the common illuminating beam path section 24.

Here too, respective collimating units 20.1 to 20.5 are mounted between the light emitting diodes and the color splitters 37.1 to 37.4, which lie closest in the beam path, and excitation filters 21.1 to 21.5 are mounted between the collimating units and the color splitters. The excitation filters 21.1 to 21.5 are configured as in the first embodiment except for the matching to the centroid wavelengths of the light emitting diodes 36.1 to 36.5.

The radiation from the common illuminating beam path section 24 reaches directly into the optic 25, which is configured in the same manner as in the first embodiment, and directs the illuminating beam onto the entry surface of the homogenizing unit 26 which is likewise configured as in the first embodiment.

In FIG. 4, the emission spectra of the light emitting diodes are shown for each of the color splitters by dotted lines and the transmission of the particular color splitter is shown as a solid line marked with the reference numeral of the color splitter. As shown in FIG. 4, the filter edges or filter flanks 38.1 to 38.4 of the color splitters are arranged monotonically decreasing along the beam path emanating from the light emitting diode 36.1 in the illuminating direction as a function of the wavelength in the same manner as the wavelength from the radiation source 36.1 to the homogenizing unit 26 of the light emitting diode 36 so that radiation of the previous light emitting diodes is passed but radiation of the next light emitting diode is deflected and is coupled into the common beam path. In the ideal case, the transmission of the color splitter in the intended pass region is 100% (T=1) and the reflectivity at 45° in the same region is 0% (R=0) and vice versa. That is: $T+R=1$.

The multiband filter of the filter cube 9 and the multiband color splitter 35 are configured in the same manner as in the first embodiment but here for the optical radiation of the five light emitting diodes.

This second embodiment is especially advantageous when the radiation of the semiconductor radiation source having the lowest characteristic emission wavelength (that is, in the example, light emitting diode 36.5) should be coupled into the homogenizing unit 26 with especially high efficiency. The reason for this is the short distance of this semiconductor radiation source to the homogenizing unit 26. Since high power light emitting diodes output the radiation with a large angle spectrum, the radiation itself can be only approximately collimated (parallelized) even with a well adapted aspheric lens. For this reason, the losses are dependent clearly on the path length which the collimated radiation must traverse.

The light emitting diodes can also be arranged in the reverse sequence, that is, in a sequence of monotone increasing centroid wavelength so that the light emitting diode 36.5 has the longest wavelength. In this case, the color splitters are to be inverted with respect to their transmission capacity, that is, transmission range and reflection range are exchanged.

This means that the color splitters are arranged in a sequence of monotone increasing flank wavelengths along the illuminating direction.

FIG. 5 shows a third embodiment which differs from the previous embodiment only by the arrangement of the semiconductor radiation sources having the collimating units and the excitation filters as well as the color splitters. The arrangement of semiconductor radiation source and the collimating unit corresponding thereto, the assigned excitation filter and the color splitter is essentially unchanged with respect to the previous embodiment except for, as required, the distances from the collimating unit to the semiconductor radiation source. Accordingly, the same reference numerals as in the previous embodiment are used. Especially, the transmission characteristics of the color splitters 37 compared to the previous embodiment are unchanged.

In this embodiment, the semiconductor radiation sources and the color splitters are so arranged that all semiconductor radiation sources are at the same distance to the last color splitter 37.4.

For this purpose, the beam paths from the semiconductor radiation sources to the common illuminating beam path section 24 are so configured that the beam path sections of two semiconductor radiation sources 36.3 and 36.4 are coupled into a common beam path section via the color splitter 37.3 which, in turn, is coupled by means of color splitter 37.2 with a beam path section leading from the semiconductor radiation source 36.1 without deflection to the common illuminating beam path section 24. The radiation of the remaining two semiconductor radiation sources 36.2 and 36.5 is coupled into the common illuminating beam section 24 via corresponding color splitters 37.1 and 37.4 forward and rearward of color splitter 37.2, respectively.

The transmission of the color splitters is shown in FIG. 6 which is analog to FIG. 4. Here, for each of the color splitters, the emission spectra of the light emitting diodes are shown by dotted lines and the transmission of the particular color splitter is shown by a solid line marked with the reference numeral of the color splitter. The flank wavelengths of the color splitters having step characteristics lie, in each case, below the emission range of the assigned light emitting diode but above the emission ranges of the light emitting diodes having emission ranges of shorter wavelengths.

As in the previous embodiments, respective excitation filters are mounted between corresponding ones of the collimating units, which follow the semiconductor radiation sources 36 in the beam path, and the color splitters closest in the beam path.

This embodiment satisfies basically the same function as the previous embodiment. The arrangement is, however, so selected that all semiconductor radiation sources have the same distance to the last color splitter or to the homogenizing unit 26. In this way, all semiconductor radiation sources can be treated in the same way with respect to the collimating optic 5 which facilitates the practical application. If the semiconductor radiation source 36.5 is moved closer to the color splitter 37.4, then the semiconductor radiation sources 36 have on average a very short distance to the homogenizing unit 26 which increases efficiency and contributes to a compact configuration.

FIG. 7 shows a fourth embodiment for the illuminating device in the examining arrangement according to the invention which differs from the previous embodiment only in the arrangement of the semiconductor radiation sources 36 and the color splitters 37. Furthermore, the color splitter 37.4 is replaced by a color splitter 37.4'. Accordingly, for the same elements, the same reference characters are used and the descriptions as to these elements for the previous embodiment apply here as well. As in the previous embodiments, the excitation filters are arranged between the collimating units 20, which follow the respective semiconductor radiation sources 36 in the corresponding beam paths and the respective color splitters 37, which are next in the beam path. Furthermore, the semiconductor radiation sources and the color splitters are also so arranged that all semiconductor radiation sources are at the same distance to the last color splitter 37.4'.

In this embodiment, the color splitters 37 form knots in a tree whose branches are radiation path sections from the semiconductor radiation sources 36 to the color splitters 37 and/or between the color splitters 37. The beam path of the semiconductor radiation source 36.5 is essentially linear.

The transmission of the color splitters is shown in FIG. 8 which is the same as in FIG. 4. In FIG. 8, the emission spectra of the light emitting diodes are shown for each color splitter by a dotted line and the transmission of the respective color splitter is shown by a solid line marked with the reference character of the color splitter. As shown in FIG. 8, the color splitter 37.4' has the inverse function compared to color splitter 37.4 and is used here in transmission for the semiconductor radiation source 36.5. This variation shows by way of example the variation possibilities for the selection of the color splitters.

The beam paths of the other semiconductor radiation sources (36.1, 36.2) and (36.3, 36.4) are coupled via color splitters 37.1 and 37.2, respectively, with the first beam path sections which, in turn, are coupled by means of color splitter 37.3 and directed to color splitter 37.4.

Figure 9:
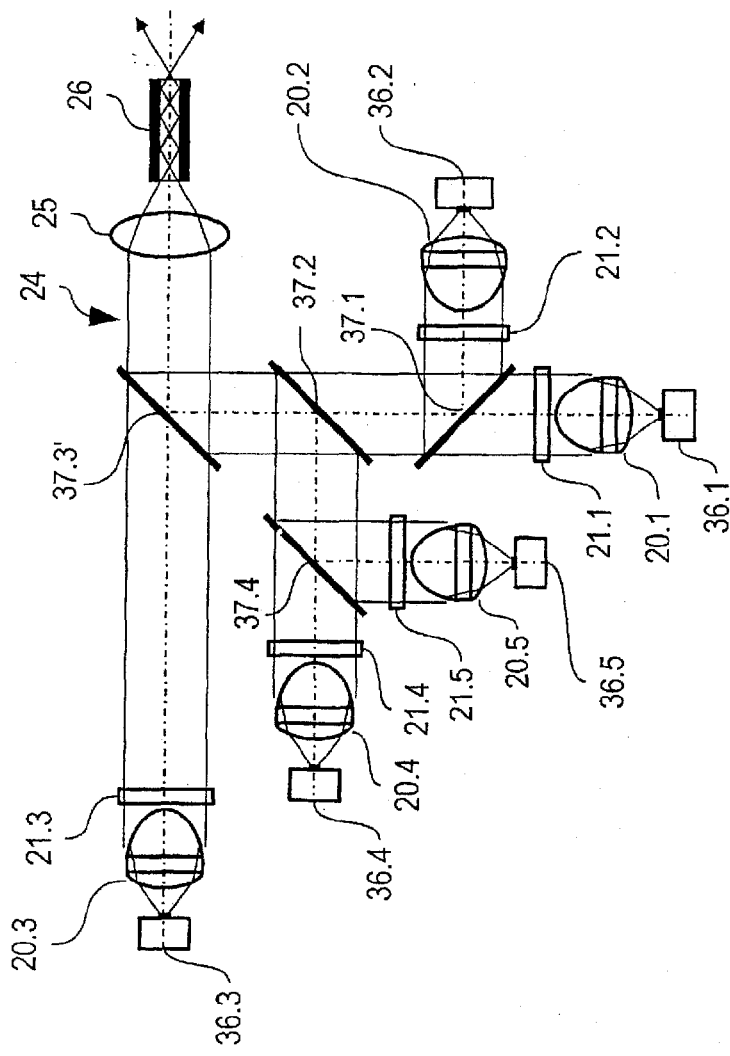
FIG. 9 shows an illuminating device of a fifth preferred embodiment of the invention.

FIG. 9 shows a fourth preferred embodiment of the illuminating device and therewith of the imaging unit of the invention and differs from the previous embodiment by the arrangement of the semiconductor radiation sources and the color splitters corresponding thereto as well as the characteristic of some of the color splitters. Therefore, for all components, the same reference characters will be used as in the first or previous embodiment.

In contrast to the previous embodiment, one of the semiconductor radiation sources 36 (in the example, the semiconductor radiation source 36.3) is so arranged that it radiates through only one of the color splitters 37, namely, the color splitter 37.3', before its radiation is coupled into the common illuminating beam path section. The emission spectrum of this one semiconductor radiation source 36 lies with its characteristic emission wavelength between at least two emission spectra or the centroid wavelengths of these emission spectra. The foregoing is especially advantageous when the semiconductor radiation source is especially weak in power in comparison to the others. According to the present state of the art, this is the case, for example, for green light emitting diodes. Additionally, the possibility is present here to arrange this semiconductor radiation source closer to the color splitter so that it can be coupled into the homogenizing unit 26 with maximum efficiency.

Figure 10:
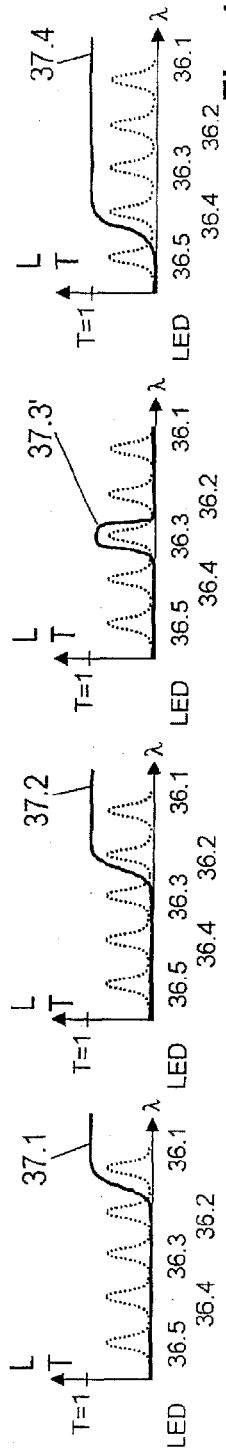
FIG. 10 shows a schematic representation of the emission spectra of the semiconductor radiation sources and of the spectral transmission performance of the color splitters of the illuminating device of FIG. 9.

The transmission of the color splitters is shown in FIG. 10 which is analog to FIG. 4. In FIG. 10, the emission spectra of the light emitting diodes are shown for each of the color splitters by dotted lines and the transmission of the particular color splitter is shown as a solid line with the line marked with the reference character of the color splitter. In contrast to the previous embodiment, the color splitter 37.3' has no step characteristic and instead operates as a bandpass for the optical radiation of the light emitting diode 36.3 assigned to this color splitter. The other color splitters are, except for the color splitter 37.4 which corresponds to that of the penultimate embodiment, unchanged relative to the previous embodiment.

Further preferred embodiments can be varied by: change of the number of semiconductor radiation sources and the number of color splitters, semiconductor radiation sources or adding semiconductor radiation sources with color splitters adapted thereto.

Figure 11:
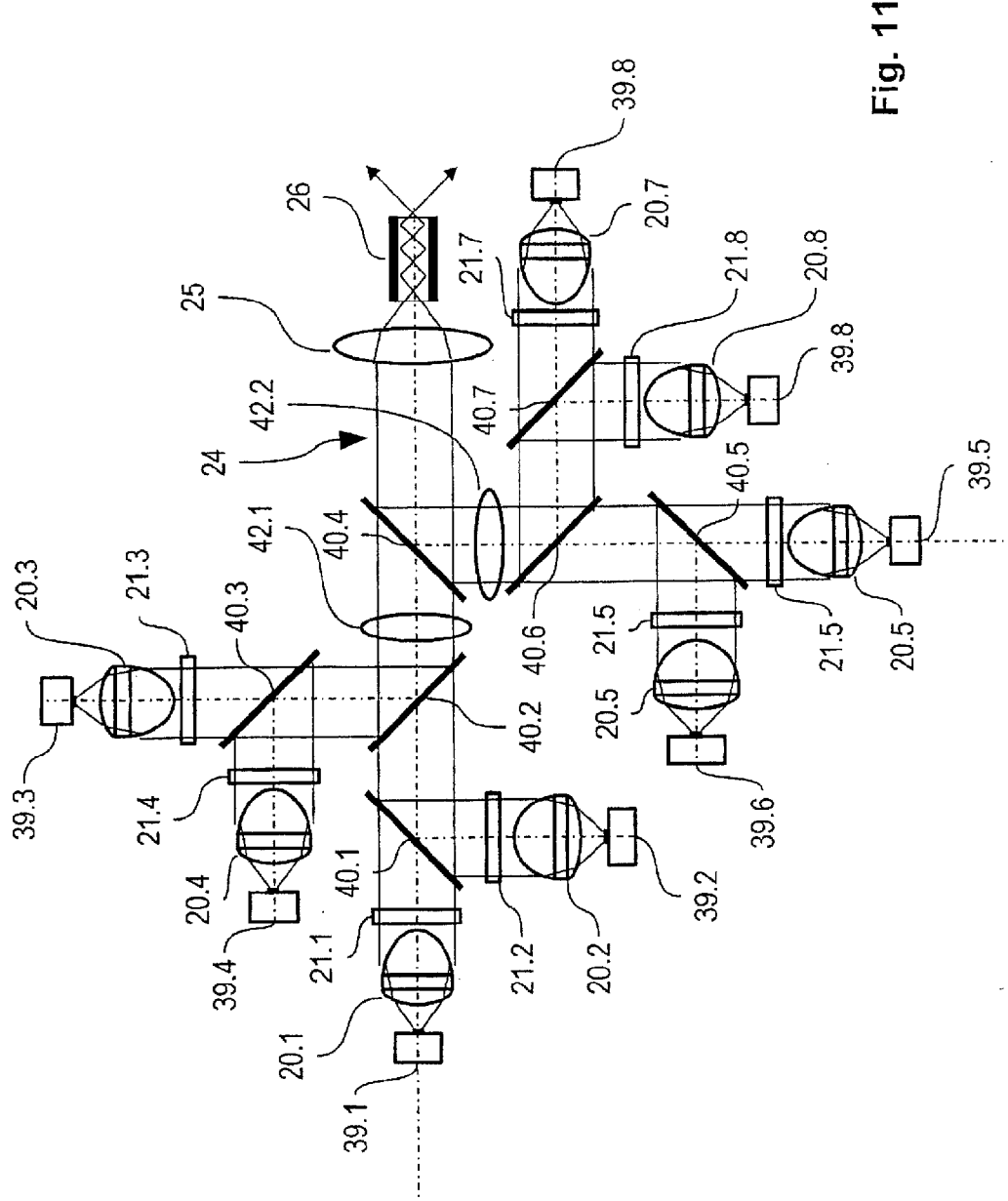
FIG. 11 shows an illuminating device according to a sixth preferred embodiment of the invention.

As a further embodiment, FIG. 11 shows an illuminating arrangement having $2^N$ semiconductor radiation sources 39.1 to 39.8 with respectively different emission spectra and $2^N-1$ color splitters 40.1 to 40.7 for N=3 wherein the semiconductor radiation sources 39 are arranged at the ends of the branches of a binary tree and thereby define leaves of the tree. The branches or knots of the tree are formed by the color splitters 40.1 to 40.7 and the transmission regions of these color splitters are spectrally arranged in the same manner as in the previous embodiments. This illuminating device is very advantageous with respect to the optimization of the energy efficiency because the illuminating device is configured to be very compact. The maximum packing density of semiconductor radiation sources can be obtained when the color splitters are arranged in a tree having $2^N$ side arms. Here too, respective collimating units 20.1 to 20.8 and excitation filters 21.1 to 21.8 are arranged between the semiconductor radiation sources and the color splitters. The excitation filters 21.1 to 21.8 are configured as interference filters and are configured in the same manner as in the second embodiment.

There are still two optional additional collimating optics 42.1 and 42.2 provided ahead of the last color splitter 40.4 which effect a still better collimation.

Even though the semiconductor radiation sources and the color splitters are arranged in a plane in the embodiments, this need not necessarily be the case. Rather, these can be rotated about sections of the overall beam path in order to achieve a best possible suitable form of the illuminating device for the application.

Figure 13:
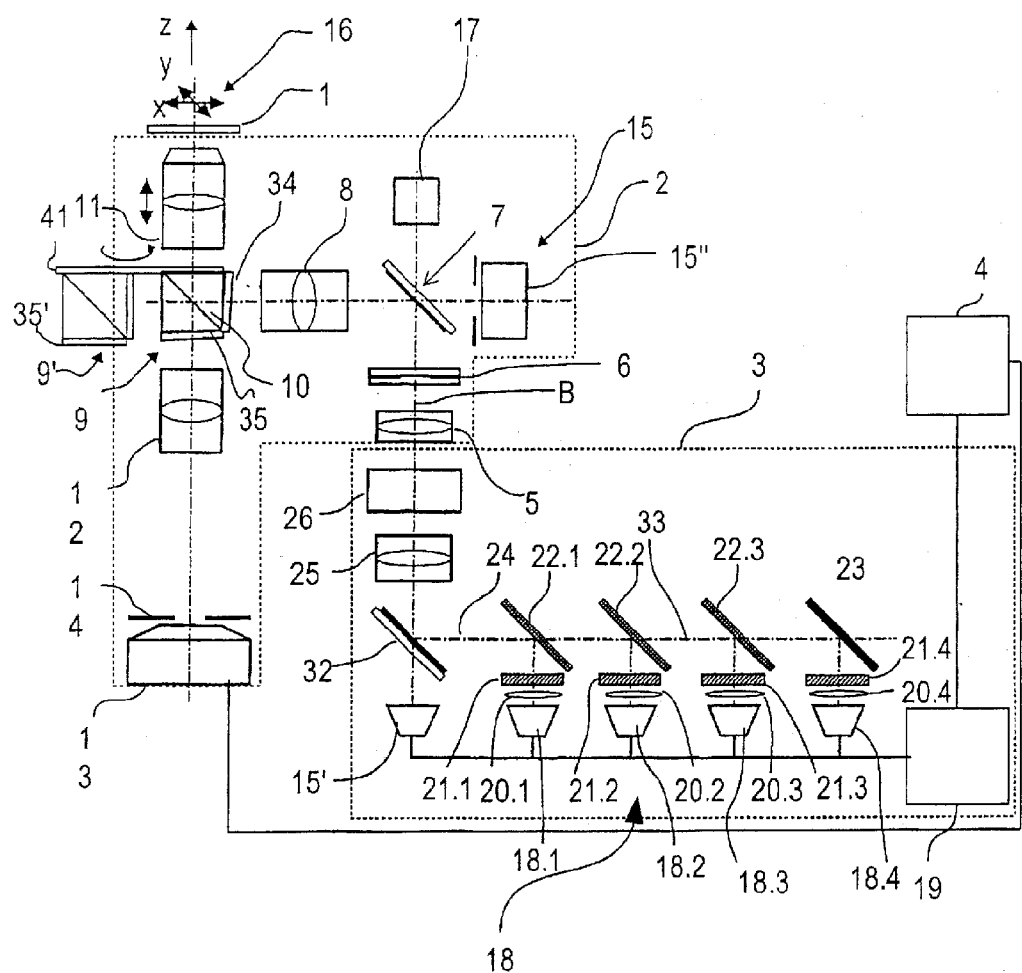

A further examining arrangement is shown schematically in FIG. 13 and differs from the examining arrangement of the first embodiment in that it has a receptacle for at least two filter cubes (9, 9') with excitation filter sets and emission filter sets by means of which each one of the filter cubes can be moved into the detection beam path of the arrangement. The filter edges of the multiband filter (35, 35') are preferably displaced relative to each other by a distance between 10 nm and 90 nm. The receptacle 41 (in the present example, a filter wheel) is preferably movable (in the example, rotatable) by means of a motorized drive (not shown in FIG. 13) in response to corresponding signals of the control and evaluation unit 4.

As a rule, more emission wavelength ranges of the illuminating device are available than are bands per multiband filter set. For this reason, a high flexibility can be obtained with the use of the filter wheel.

A further preferred embodiment of an illuminating device differs from the illuminating device of FIG. 1 in that operator-controlled elements, for example, switches, are provided on a housing of the illuminating device by means of which the semiconductor radiation sources can be switched on and off individually or in combination.

FIGS. 12b and 12c show two additional alternatives for the collimating units for otherwise unchanged illuminating devices of the previous embodiments.

In FIG. 12b, a diffractive or holographic element 43 is provided in addition to an aspheric lens 29 on the light emitting diode chip 28. The element 43 increases the radiation yield of the light emitting diode in that it better couples the radiation into the aspheric lens 29.

In FIG. 12c, a radiation concentrator or light concentrator 44 of plastic or glass is mounted in the beam path ahead of the light emitting diode in lieu of the aspheric lens 29. The concentrator 44 collimates the light entering the concentrator via total reflection at the boundary surfaces of the light concentrator.

Another preferred embodiment differs from the second embodiment by the configuration of one of the semiconductor radiation sources. In order to be able to make available an optical radiation in the wavelength range about 570 nm, a light emitting diode is used to output blue light or a light emitting diode is used to output UV radiation. The light emitting diode contains luminescent substances which lead to a radiation emission in the desired spectral range. The UV light or blue light of the light emitting diode is converted via fluorescence or phosphorescence into light in the desired wavelength range, that is, of another color.

The above-mentioned examining arrangements can be used for determining the concentration of the pregiven fluorescence colorants. The filter bands and the characteristic emission wavelengths are so matched to each other that the fluorescence excitation and fluorescence detection are as efficient as possible for the pregiven fluorescence colorant.

If the excitation spectra and fluorescence spectra are known for M (M positive natural number) fluorescence colorants as well as the emission spectra of the semiconductor radiation sources and the filters, then the concentrations of the M fluorescence colorants in the specimen 1 can basically be determined with M spectrally different measurements. In order to obtain spectrally different measurements, at least one excitation wavelength or one fluorescence wavelength must be different than in the remaining measurements. From the excitation standpoint, this can be realized via switching on or switching off of the individual semiconductor radiation sources. Another possibility is to exchange the multiband filter set.

Preferably, however, several excitation wavelengths are used simultaneously for the measurements by switching on at least two of the semiconductor radiation sources.

The examining arrangement of the first embodiment can especially be used for carrying out a preferred embodiment of the method of the invention for measuring the concentration of a number M of pregiven fluorescence colorants in the specimen 1. Here, M measurements are carried out. For each of the measurements, another number less than or equal to M of emission wavelength ranges is used which corresponds to the excitation spectra of the fluorescence colorants for forming excitation radiation. The specimen is irradiated with the excitation radiation and the resultant fluorescence radiation is detected. The concentration of the fluorescence colorants is determined from the detection results of the M measurements.

This is described for the example of a specimen with M=3 pregiven fluorescence colorants, in the example, FITC, CY3 and Cy5.

For this purpose, a 3-band filter set is used, for example, the filter set 61005 of the Chroma Technology Company. With each additional measurement, a further emission band is used in addition to the emission bands used in the previous measurement, that is, successively more emission bands are used for the measurements. Accordingly, in the first measurement, only one semiconductor radiation source (in the example, the blue light emitting diode) is switched on. In the second measurement, an additional semiconductor source is switched on so that the blue and the green light emitting diodes are used. In the third measurement, a still further emission spectrum is included by switching on the third semiconductor radiation source (in the example, the red light emitting diode) so that all three light emitting diodes operate and emission radiation or excitation radiations in the blue, green and red range are simultaneously available.

The three measurements supply a linear equation system with concentrations for the three fluorescence colorants as unknown variables. The equation system is tri-diagonal and can clearly be solved with known mathematical methods (see, for example, William H. Press, Saul A. Teukolsky, William T. Vetterling: "Numerical Receipes in C", 2nd edition, Cambridge University Press 1999, ISBN: 0521431085) and the concentration ratios can thereby be determined. Cross talk effects are eliminated which could occur when using several excitation bands.

The accuracy of the concentration determination can be increased with further measurements, especially, with other excitation wavelengths.

For this purpose, especially a filter set can be used wherein all filter edges are shifted by several 10 nm to higher or lower wavelengths relative to the first filter set. In this way, other regions of the excitation spectra and emission spectra of the fluorescence colorants are utilized which supply additional information.

The advantages of the illuminating device of the invention explained for microscopy can also be used for other applications. For example, the illuminating device can be used as illumination for digital projection systems when an especially extensive color space is to be covered. A use for general illuminating purposes is likewise conceivable when a rapid variability of the color spectrum is a consideration. Especially, optical devices for examining the eye or devices for examining human or animal tissue, for example, surgical microscopes or arrangements for examining the eye such as fundus cameras, can be equipped with an illuminating device according to one of the above embodiments.

The illuminating device permits a color true illustration by means of color management insofar as a viewing or detection in reflection takes place. Color management is understood to mean especially that in the arrangement, the illuminating device and an image detecting unit for detecting images of an object, which arise under illumination by the illuminating device, the spectral characteristics of the illuminating device and the image detection unit are so matched to each other that for a human viewer, the same colors result as in the viewing with the eye under a standard illumination, for example, a halogen lamp having a pregiven color temperature, for example, of 3200 K.

The invention claimed is:

1. An illuminating device comprising:
at least four semiconductor radiation sources for emitting optical radiation in respectively different emission wavelength ranges and along respective beam path segments;
at least one color splitter assigned to each of at least three of said semiconductor radiation sources;
each of said color splitters being reflective for the optical radiation of the semiconductor radiation source corresponding thereto;
at least one of said semiconductor radiation sources having at least one luminescence substance for color conversion;
said semiconductor radiation sources and said color splitters being so arranged that the optical radiation emitted by each of said semiconductor radiation sources is coupled into a common illuminating beam path segment;
a plurality of collimating units mounted in said beam path segments, respectively, to collimate the optical radiation emitted by corresponding ones of said semiconductor radiation sources and passing to respective ones of said color splitters;
wherein at least one color splitter is reflective for the optical radiation of at least two semiconductor radiation sources;
a partially transparent deflecting mirror being provided in said common illuminating beam path segment;
a monitor detector being arranged to receive light transmitted by said partially transparent deflecting mirror; and,
an evaluation unit determining a light intensity reflected by said partially transparent deflecting mirror from a signal received by said monitor detector.

2. The illuminating device of claim 1, further comprising a bandpass filter arranged between said one semiconductor radiation source and the collimating unit corresponding thereto; and, said bandpass filter being configured to spectrally limit the radiation of said one semiconductor radiation source to a suitable wavelength range.

3. The illuminating device of claim 1, further comprising a control unit for switching said semiconductor radiation sources on and off independently of each other.

4. The illuminating device of claim 3, wherein said control unit is so configured that said emission radiation powers of said semiconductor radiation sources are adjustable independently of each other.

5. The illuminating device of claim 1, wherein said semiconductor radiation sources are overall five to eight in number and have respectively different emission wavelength ranges.

6. The illuminating device of claim 1, wherein the beam path segments from the semiconductor radiation sources up to directly behind the last color splitter form a binary tree.

7. The illuminating device of claim 1, wherein at least one of said collimating units includes an aspheric lens or an aspheric mirror.

8. The illuminating device of claim 1, further comprising a bandpass filter mounted in one of said beam path segments between the collimating unit and the color splitter corresponding thereto.

9. The illuminating device of claim 1, wherein three of said color splitters are mounted in the same beam path segment; and, said color splitters have respective filter edges at wavelengths which monotonically increase or decrease along said same beam path segment.

10. The illuminating device of claim 1, further comprising a homogenizing unit mounted in said common illuminating beam path segment downstream of said color splitters.

11. The illuminating device of claim 1, further comprising a plurality of optical elements mounted downstream of said semiconductor radiation sources; and, said semiconductor radiation sources and said optical elements having light conductance values adapted to each other for maximizing the energy flow of the radiation to be emitted.

12. The illuminating device of claim 1, further comprising a control unit configured to cause at least two of said semiconductor radiation sources to generate white light of variable color temperature by additive color mixing of the optical radiation emitted by said at least two semiconductor radiation sources.

13. An optical arrangement comprising:
an optical assembly defining an optical axis;
an illuminating device for supplying optical radiation along an illuminating beam path;
means for coupling said optical radiation into said optical assembly for transmission along said optical axis; and, said illuminating device including:

at least four semiconductor radiation sources for emitting optical radiation in respectively different emission wavelength ranges and along respective beam path segments;

at least one color splitter assigned to each of at least three of said semiconductor radiation sources;

each of said color splitters being reflective for the optical radiation of the semiconductor radiation source corresponding thereto;

at least one of said semiconductor radiation sources having at least one luminescence substance for color conversion;

said semiconductor radiation sources and said color splitters being so arranged that the optical radiation emitted by each of said semiconductor radiation sources is coupled into a common illuminating beam path segment;

a plurality of collimating units mounted in said beam path segments, respectively, to collimate the optical radiation emitted by corresponding ones of said semiconductor radiation sources and passing to respective ones of said color splitters;

wherein at least one color splitter is reflective for the optical radiation of at least two semiconductor radiation sources;

a partially transparent deflecting mirror being provided in said common illuminating beam path segment;

a monitor detector being arranged to receive light transmitted by said partially transparent deflecting mirror; and, an evaluation unit determining a light intensity reflected by said partially transparent deflecting mirror from a signal received by said monitor detector.

14. The optical arrangement of claim 13, further comprising a bandpass filter arranged between said one semiconductor radiation source and the collimating unit corresponding thereto; and, said bandpass filter being configured to spectrally limit the radiation of said one semiconductor radiation source to a suitable wavelength range.

15. The optical arrangement of claim 13, wherein said optical arrangement is configured to examine a specimen.

16. The optical arrangement of claim 15, wherein said optical arrangement is configured as a wide field microscope or a fluorescence reader.

17. The optical arrangement of claim 15, wherein said optical arrangement is configured to conduct fluorescence examinations of said specimen and said optical assembly defines a detection beam path along which fluorescence radiation emanating from said specimen travels; and, said means includes at least one multiband emission filter or multiband emission filter set arranged in said detection beam path for said fluorescence radiation.

18. The optical arrangement of claim 17, wherein said multiband emission filter is contained in a filter cube which further includes a multiband excitation filter or multiband excitation filter set and a multiband color splitter for deflecting said illuminating radiation of said illuminating device or said fluorescence radiation emanating from said specimen with said multiband excitation filter or said multiband excitation filter set being mounted in said illuminating beam path of said illuminating device.

19. The optical arrangement of claim 17, wherein at least one of the emission spectra of said illuminating device lies with its characteristic wavelength between two emission wavelength ranges of said multiband emission filter.

20. The optical arrangement of claim 18, wherein said multiband excitation filter is a first multiband excitation filter and said optical arrangement further includes a second multiband excitation filter; and, said multiband excitation filters have filter edges shifted relative to each other by a distance of between 10 nm and 90 nm.

21. The optical arrangement of claim 20, further comprising a receptacle for at least two filter cubes by means of which one of the filter cubes is movable into said detection beam path.

22. A method for measuring the concentration of a number M of pregiven fluorescence colorants in a specimen utilizing a fluorescence examining arrangement to conduct M measurements therewith, the fluorescence examining arrangement including: an optical assembly defining a detection beam path along which fluorescence radiation emanating from said specimen travels; an illuminating device for supplying optical radiation along an illuminating beam path; means for coupling said optical radiation into said optical assembly for transmission along said path; and, said illuminating device including: at least four semiconductor radiation sources for emitting optical radiation in respectively different emission wavelength ranges and along respective beam path segments; at least one color splitter assigned to each of at least three of said semiconductor radiation sources; each of said color splitters being reflective for the optical radiation of the semiconductor radiation source corresponding thereto; at least one of said semiconductor radiation sources having at least one luminescence substance for color conversion; said semiconductor radiation sources and said color splitters being so arranged that the optical radiation emitted by each of said semiconductor radiation sources is coupled into a common illuminating beam path segment; a plurality of collimating units mounted in said beam path segments, respectively, to collimate the optical radiation emitted by corresponding ones of said semiconductor radiation sources and passing to respective ones of said color splitters; and, said means including at least one multiband emission filter or multiband emission filter set arranged in said detection beam path for said fluorescence radiation; and, said method comprising the steps of:

for each of the measurements, using another number less than or equal to M of emission wavelength ranges for forming the excitation radiation with said emission wavelength ranges corresponding to the excitation spectra of said fluorescence colorants;

irradiating said specimen with said excitation radiation and detecting the resulting fluorescence radiation;

from the detection results of the M measurements, determining the concentration of said fluorescence colorants;

wherein at least one color splitter is reflective for the optical radiation of at least two semiconductor radiation sources;

providing a partially transparent deflecting mirror in said common illuminating beam path segment;

arranging a monitor detector to receive light transmitted by said partially transparent deflecting mirror; and, determining a light intensity reflected by said partially transparent deflecting mirror from a signal received by said monitor detector.

* * * * *